US011692978B2

(12) United States Patent
Cui et al.

(10) Patent No.: US 11,692,978 B2
(45) Date of Patent: Jul. 4, 2023

(54) VOC MARKERS IN SALIVA FOR DIAGNOSIS OF GASTRIC CANCER AND GASTRIC CANCER DIAGNOSTIC METHOD USING SAME

(71) Applicant: Shanghai Jiao Tong University, Shanghai (CN)

(72) Inventors: Daxiang Cui, Shanghai (CN); Cuili Xue, Shanghai (CN); Yunsheng Chen, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 372 days.

(21) Appl. No.: 16/862,617

(22) Filed: Apr. 30, 2020

(65) Prior Publication Data
US 2020/0348269 A1    Nov. 5, 2020

(30) Foreign Application Priority Data

Apr. 30, 2019   (CN) .......................... 201910362235.8

(51) Int. Cl.
| | |
|---|---|
| *G01N 30/06* | (2006.01) |
| *G01N 1/22* | (2006.01) |
| *G01N 30/72* | (2006.01) |
| *A61B 10/00* | (2006.01) |
| *A61B 5/08* | (2006.01) |

(52) U.S. Cl.
CPC ......... *G01N 30/06* (2013.01); *A61B 10/0051* (2013.01); *G01N 1/2226* (2013.01); *G01N 30/7206* (2013.01); *A61B 5/082* (2013.01); *G01N 2001/2229* (2013.01)

(58) Field of Classification Search
CPC .. G01N 30/06; G01N 1/2226; G01N 30/7206; G01N 2001/2229; A61B 10/0051; A61B 5/082
USPC ......................................................... 436/161
See application file for complete search history.

(56) References Cited

U.S. PATENT DOCUMENTS

| | | | | |
|---|---|---|---|---|
| 2009/0170100 A1* | 7/2009 | Chow | ................. | C07K 14/205 435/6.12 |
| 2012/0126111 A1* | 5/2012 | Chaubron | ........ | G01N 33/57488 250/282 |
| 2014/0244229 A1* | 8/2014 | Zhang | ...................... | G16B 5/00 703/11 |

(Continued)

FOREIGN PATENT DOCUMENTS

| | | | | |
|---|---|---|---|---|
| CN | 101750491 A | | 6/2010 | |
| CN | 102495146 A | * | 6/2012 | ......... G01N 30/8686 |

(Continued)

OTHER PUBLICATIONS

Translation CN-103940924-A (Year: 2014).*

*Primary Examiner* — Alexander A Mercado
*Assistant Examiner* — Monica S Young

(57) ABSTRACT

Disclosed herein are a group of gastric cancer VOC markers in saliva and an application thereof in the preparation of a diagnostic reagent of gastric cancer. The markers are a combination of compounds selected from the group consisting of acetaldehyde, 2-methylbutyraldehyde, isopropanol, hexanal, n-butanol, cineole, nonanal, menthone, 2-ethylhexanol, menthol, anethole and dodecanol. The diagnostic reagent is used for detecting the contents of the marker in a saliva sample of a subject to perform the diagnosis of gastric cancer.

2 Claims, 1 Drawing Sheet

(56) References Cited

U.S. PATENT DOCUMENTS

2016/0258910 A1* 9/2016 Grandy .................. G01N 30/08
2016/0356777 A1* 12/2016 Kim ................. G01N 33/57446

FOREIGN PATENT DOCUMENTS

| | | | | | |
|---|---|---|---|---|---|
| CN | 102495146 | A | | 6/2012 | |
| CN | 103940924 | A | | 7/2014 | |
| CN | 103940924 | A | * | 7/2014 | |
| CN | 104297355 | A | | 1/2015 | |
| CN | 104634907 | A | | 5/2015 | |
| CN | 104634907 | A | * | 5/2015 | |
| CN | 105699514 | A | | 6/2016 | |
| CN | 105699514 | A | * | 6/2016 | |
| CN | 106324118 | A | | 1/2017 | |
| CN | 107192704 | A | | 9/2017 | |
| CN | 107884491 | A | * | 4/2018 | |
| CN | 107884491 | A | | 4/2018 | |
| CN | 108152508 | A | | 6/2018 | |
| CN | 108700563 | A | * | 10/2018 | ............. G01N 30/72 |
| CN | 111602055 | A | * | 8/2020 | ........... G01N 33/497 |
| WO | 2015093800 | A1 | | 6/2015 | |

* cited by examiner

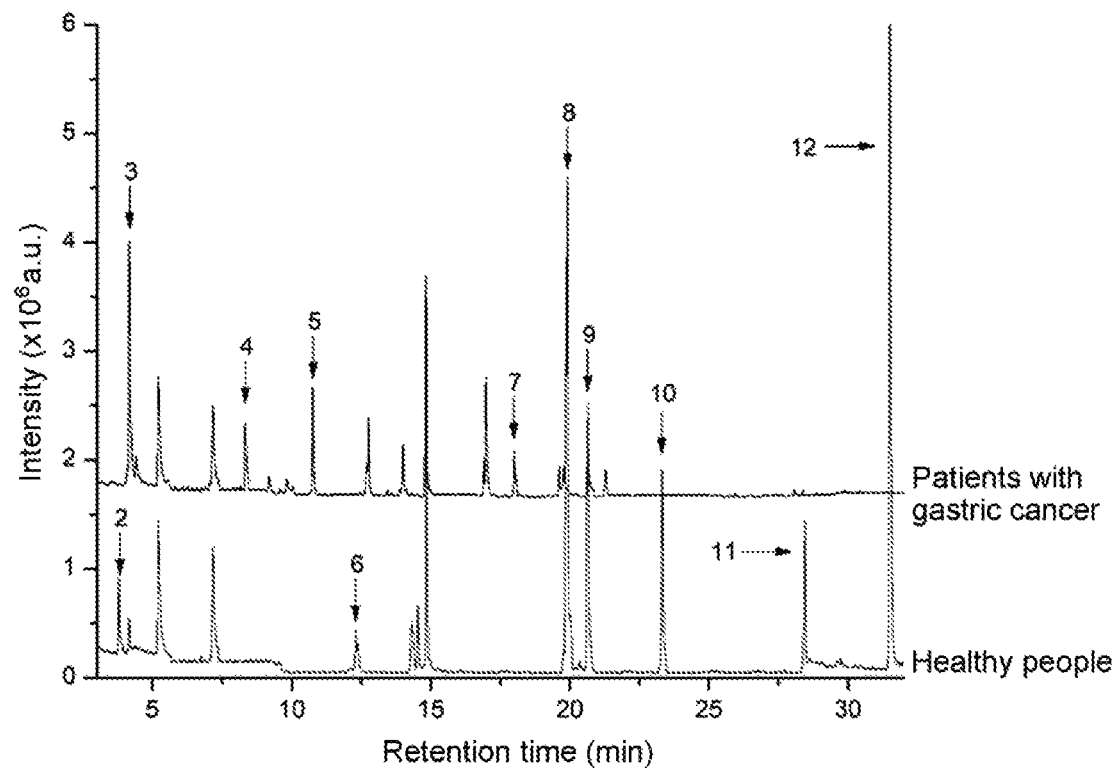

VOC MARKERS IN SALIVA FOR DIAGNOSIS OF GASTRIC CANCER AND GASTRIC CANCER DIAGNOSTIC METHOD USING SAME

CROSS-REFERENCE TO RELATED APPLICATIONS

This application claims the benefit of priority from Chinese Patent Application No. 201910362235.8, filed on Apr. 30, 2019. The content of the aforementioned application, including any intervening amendments thereto, is incorporated herein by reference.

TECHNICAL FIELD

This application relates to the diagnosis of gastric cancer, and more particularly to VOC (volatile organic compound) markers in saliva for the diagnosis of gastric cancer and gastric cancer diagnostic method using the same.

BACKGROUND

Gastric cancer is the fourth most common cancer with the second-highest cancer-related mortality in the world, and nearly 50% of the diagnostic cases occur in China. Since the gastric cancer has a long incubation period and no obvious symptoms in the early stage, most cases have developed to advanced stage when diagnosed, and the optimal treatment opportunity is missed, resulting in poor prognosis, easy metastasis and low median overall survival (OS) rate (less than 1 year). Traditional cancer diagnostic methods mainly include endoscopy and biopsy. However, these methods fail to achieve the timely and rapid diagnosis for gastric cancer due to frequent occurrence of missed diagnosis, great pain to patients, high cost and high requirements for the operator.

Currently, some metabolites, genes and proteins in body fluids (such as saliva, blood and urine) have been found to be related to specific cancers, and these substances may play an important role in overcoming the limitations of traditional diagnostic methods and achieving the rapid and accurate diagnosis. With regard to most cancers, their specific gene and protein markers in body fluids generally have the defects of complicated detection process, low detection sensitivity and specificity. In addition, compared to blood and urine, saliva has simpler composition and smaller matrix effects (such as blood cells and aggregation in blood). And saliva also has the advantages of rapid collection, non-invasion, low cost, easy storage and transportation. It has been demonstrated that volatile organic compounds (VOCs) can be used as a source of diagnostic information for many local and systemic diseases, such as cancer, diabetes and liver disease, and the VOCs are stable in property and rich in variety. Therefore, the VOCs in saliva can be used as markers in the early diagnosis and screening of gastric cancer, allowing for rapid, non-invasive, economical and effective diagnosis. Currently, it has rarely been investigated about the VOCs in saliva as diagnostic biomarkers for gastric cancer. And due to the lack of biomarkers species, low detection specificity and low diagnosis accuracy, the application of VOCs as markers in clinical diagnosis is greatly limited.

SUMMARY

An object of the invention is to provide a group of VOC markers in saliva for the diagnosis of gastric cancer and an application thereof in the preparation of diagnostic reagents for gastric cancer to overcome the defects in the prior art.

Principles of the invention are described as follows. Gastric cancer tissues can produce some specific volatile organic compounds, and part of them will enter the blood and pass through the intercellular space through the extracellular or paracellular matrix to finally reach the saliva. Then the volatile organic compounds in the saliva can be extracted and used as markers in the diagnosis of gastric cancer, which provides an effective and non-invasive means to monitor health status, disease occurrence and progression and therapeutic effects.

Technical solutions of the invention are described as follows.

In a first aspect, the invention provides a group of VOC markers for the diagnosis of gastric cancer, wherein the VOC markers are a combination of volatile organic compounds selected from the group consisting of acetaldehyde (CAS No. 75-07-0), 2-methylbutyraldehyde (CAS No. 96-17-3), isopropanol (CAS No. 67-63-0), hexanal (CAS No. 66-25-1), n-butanol (CAS No. 71-36-3), cineole (CAS No. 470-82-6), nonanal (CAS No. 124-19-6), menthone (CAS No. 491-07-6), 2-ethylhexanol (CAS No. 104-76-7), menthol (CAS No. 1490-04-6), anethole (CAS No. 104-46-1) and dodecanol (CAS No. 112-53-8). The diagnosis of gastric cancer is performed by determining the contents of the VOC markers in saliva of a subject.

In an embodiment, the determination of the contents of the VOC markers in saliva of the subject is performed by GC-MS.

In an embodiment, in the case that three compounds of acetaldehyde, isopropanol, hexanal, n-butanol and nonanal are present and at least three compounds of menthone, menthol, anethole and dodecanol are absent in the saliva, the subject is diagnosed with gastric cancer; and in the case that 2-methylbutyraldehyde, cineole and 2-ethylhexanol undergo significant decrease in contents, the subject is preliminarily diagnosed with gastric cancer.

In an embodiment, the VOC markers are a combination of acetaldehyde, 2-methylbutyraldehyde, isopropanol, hexanal, n-butanol, cineole, nonanal and 2-ethylhexanol;

a combination of 2-methylbutyraldehyde, cineole, menthone, 2-ethylhexanol, menthol, anethole and dodecanol;

a combination of acetaldehyde, isopropanol, hexanal, n-butanol, nonanal, menthone, menthol, anethole and dodecanol;

a combination of isopropanol, hexanal, n-butanol, nonanal, menthone, 2-ethylhexanol and menthol; or a combination of acetaldehyde, 2-methylbutyraldehyde, isopropanol, hexanal, n-butanol, cineole, nonanal, menthone, 2-ethylhexanol, menthol, anethole and dodecanol.

In a second aspect, the invention provides a method of diagnosing gastric cancer in a subject, comprising:
obtaining a saliva sample from the subject;
measuring the VOC markers in the saliva sample; and
determining whether the subject suffers from gastric cancer or not according to the measured results;
wherein the VOC markers is a combination of volatile organic compounds selected from the group consisting of acetaldehyde, 2-methylbutyraldehyde, isopropanol, hexanal, n-butanol, cineole, nonanal, menthone, 2-ethylhexanol, menthol, anethole and dodecanol.

In a third aspect, the invention further provides a system for detecting VOC markers for the diagnosis of gastric cancer, comprising a saliva collecting device, a headspace sampling device, a solid-phase microextraction device and a gas chromatography-mass spectrometer (GC-MS); wherein a saliva sample collected by the saliva collecting device is injected through the headspace sampling device and concentrated by a solid-phase microextraction device, and then transferred to the GC-MS for the determination of the contents of the VOC markers; and the VOC markers are a combination of acetaldehyde, 2-methylbutyraldehyde, isopropanol, hexanal, n-butanol, cineole, nonanal, menthone, 2-ethylhexanol, menthol, anethole and dodecanol.

Compared to the prior art, the invention has the following beneficial effects.

1. The diagnosis method provided herein has the advantages of rapid sample collection, non-invasive operation, low cost, easy storage and easy transportation.

2. There are many volatile organic compounds to be detected included in the gastric cancer markers, which ensures high accuracy of the diagnosis.

3. There are significant differences in the gastric cancer markers between the saliva samples of the gastric cancer group and the healthy control group which ensures accurate and reliable diagnostic results.

BRIEF DESCRIPTION OF THE DRAWINGS

The FIGURE shows the GC-MS detection results of gastric cancer markers in saliva samples respectively from a patient with gastric cancer and a healthy control.

DETAILED DESCRIPTION OF EMBODIMENTS

The invention will be described in detail below with reference to the accompanying drawings and embodiments.

Example 1 Collection of Saliva Samples

Gastric cancer VOC markers in a saliva sample were screened by analyzing the saliva samples from the patients with gastric cancer and healthy people, where a total of 90 saliva samples were collected, including 36 samples from the patients with gastric cancer and 54 samples from healthy people.

The participants all did not have other malignancies, blood diseases or metabolic system diseases.

Those with gastric cancer were clinically diagnosed by biopsy, computed tomography (CT) and puncture, and did not receive chemotherapy or other treatment before the saliva collection.

Before the collection, each participant was required to keep a natural and calm mood within 48 h and to avoid smoking and drinking alcohol within 24 h. Within 1 h before the sample collection, all participants were prohibited from ingesting any food to keep the mouth clean.

All participants were required to gargle with pure water before the sample collection, and to collect 4-6 mL of a saliva sample 5 min after the gargling.

Example 2 Analysis of Saliva Samples 1 mL of the collected saliva sample was accurately pipetted, transferred to a vial and heated for about 20 min to 80° C. to achieve the chemical equilibrium of the vapor.

The headspace sampling device was connected to the solid-phase microextraction (SPME) device. A 75 µm CAR/PDMS-coated SPME fiber was used to pre-concentrate VOCs in the saliva sample, where the pre-concentration lasted for 30-35 min.

The GC-MS analysis was performed as follows. The SPME fiber was inserted into an injection port and heated at 280° C. for 1 min for desorption, and a splitless injection was chosen. 2 min later, a splitting valve was opened. A CD-1MS chromatographic column (1.4 µm×60 m×0.25 mm) was employed.

The temperature was programmed as follows: 35° C. for 10 min; rise to 200° C. at 8° C./min; rise to 220° C. at 15° C./min; and 220° C. for 12 min.

Full scanning range: 42-400 amu; Electron impact energy: 70 eV; Quadrupole mass spectrometer ion source temperature: 200° C.; Carrier gas: He; and flow rate: 44.2 cm/s.

The detected volatile organic compounds were preliminarily identified according to the NIST08 library, and those with a similarity larger than 90% were further quantified according to the corresponding peak areas. The GC-MS analysis results of the saliva samples from the patients with gastric cancer and the healthy controls were shown in the FIGURE, and the corresponding gastric cancer VOC markers were presented in Table 1.

TABLE 1

Gastric cancer markers in saliva samples from the patients with gastric cancer and the healthy controls

| Peak | Compounds |
|---|---|
| 1 | Acetaldehyde |
| 2 | 2-Methylbutyraldehyde |
| 3 | Isopropanol |
| 4 | Hexanal |
| 5 | n-Butanol |
| 6 | Cineole |
| 7 | Nonanal |
| 8 | Menthone |
| 9 | 2-Ethylhexanol |
| 10 | Menthol |
| 11 | Anethole |
| 12 | Dodecanol |

It can be seen from the FIGURE and Table 1 that levels of nonanal, acetaldehyde, isopropanol, hexanal and n-butanol in the saliva samples of the patients with gastric cancer were significantly higher than those in the saliva samples of the healthy controls, while the levels of 2-methylbutanal, cineole and 2-ethylhexanol were relatively lower in the saliva samples of the patients with gastric cancer. It should be further noted that menthone, menthol, anethole and dodecanol were only present in the saliva of healthy people. Therefore, such 12 volatile organic compounds were suitable as markers to be applied to the diagnosis of gastric cancer, allowing for more accurate diagnosis.

Example 3

The screened VOC markers were applied in the rapid diagnosis of gastric cancer for validation.

10 saliva samples from patients with gastric cancer and 10 saliva samples from healthy people were collected. When three compounds of acetaldehyde, isopropanol, hexanal, n-butanol and nonanal were present and at least three compounds of menthone, menthol, anethole and dodecanol were absent, the subject was diagnosed with gastric cancer; and when 2-methylbutanal, cineole and 2-ethylhexanol underwent significant decrease in content, the subject was preliminarily diagnosed with gastric cancer. Otherwise, the subject was considered to be healthy. The detection process was the same as that in Examples 1 and 2. The results showed that there were 8 gastric cancer samples and 9 normal samples that met the above criteria, indicating that the accurate rate of the diagnosis involving the use of such markers was greater than 80%.

The above-mentioned embodiments are merely illustrative of the invention, and are not intended to limit the invention. Any change, replacement, modification and simplification made by those skilled in the art without departing from the spirit of the invention should still fall within the scope of the invention defined by the appended claims.

What is claimed is:

1. A method of diagnosing gastric cancer in a subject, the method comprising steps of:
    a) obtaining a saliva sample from the subject;
    b) detecting volatile organic compound (VOC) markers in the saliva sample by:
        concentrating the VOC markers in the saliva sample using a solid-phase microextraction device; and
        performing an analysis using a gas chromatography-mass spectrometry under a temperature program of 35° C. for 10 minutes (min), rise to 200° C. at a rate of 8° C./min, rise to 220° C. at a rate of 15° C./min and 220° C. for 12 min,
        wherein the VOC markers are compounds selected from the group consisting of acetaldehyde, isopropanol, hexanal, n-butanol, nonanal, menthone, menthol, anethole, dodecanol, and a combination thereof; and
    c) diagnosing the subject with gastric cancer when at least three of the compounds of acetaldehyde, isopropanol, hexanal, n-butanol and nonanal are present and at least three of the compounds of menthone, menthol, anethole and dodecanol are absent in the saliva sample.

2. A method of diagnosing gastric cancer in a subject, the method comprising steps of:
    a) obtaining a saliva sample from the subject;
    b) detecting volatile organic compound (VOC) markers in the saliva sample by:
        concentrating the VOC markers in the saliva sample using a solid-phase microextraction device; and
        performing an analysis using a gas chromatography-mass spectrometry under a temperature program of 35° C. for 10 min, rise to 200° C. at a rate of 8° C./min, rise to 220° C. at a rate of 15° C./min and 220° C. for 12 min,
        wherein the VOC markers are compounds selected from the group consisting of acetaldehyde, isopropanol, hexanal, n-butanol, nonanal, menthone, menthol, anethole, dodecanol, and a combination thereof;
    c) preliminarily diagnosing the subject with gastric cancer when significant increase in content of 2-methylbutyraldehyde, cineole and 2-ethylhexanol is detected; and
    d) diagnosing the subject with gastric cancer when at least three of the compounds of acetaldehyde, isopropanol, hexanal, n-butanol and nonanal are present and at least three of the compounds of menthone, menthol, anethole and dodecanol are absent in the saliva sample.

* * * * *